(12) United States Patent
Mori et al.

(10) Patent No.: US 10,041,924 B2
(45) Date of Patent: Aug. 7, 2018

(54) CONCENTRATION-FACTOR MEASUREMENT DEVICE AND METHOD

(71) Applicant: KURITA WATER INDUSTRIES LTD., Tokyo (JP)

(72) Inventors: Shintarou Mori, Tokyo (JP); Yukimasa Shimura, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 33 days.

(21) Appl. No.: 15/304,762

(22) PCT Filed: Apr. 1, 2015

(86) PCT No.: PCT/JP2015/060318
§ 371 (c)(1),
(2) Date: Oct. 17, 2016

(87) PCT Pub. No.: WO2015/159710
PCT Pub. Date: Oct. 22, 2015

(65) Prior Publication Data
US 2017/0038358 A1    Feb. 9, 2017

(30) Foreign Application Priority Data

Apr. 18, 2014 (JP) ................................. 2014-086543

(51) Int. Cl.
*G01N 33/18* (2006.01)
*G01N 21/59* (2006.01)
*G01N 27/06* (2006.01)

(52) U.S. Cl.
CPC ......... *G01N 33/1853* (2013.01); *G01N 21/59* (2013.01); *G01N 27/06* (2013.01); *G01N 33/182* (2013.01)

(58) Field of Classification Search
CPC ......... G01N 33/18; G01N 21/59; G01N 27/26
See application file for complete search history.

(56) References Cited

U.S. PATENT DOCUMENTS 7,702,473 B2 * 4/2010 Widder ................ G01N 33/186
702/50
9,557,309 B2 * 1/2017 Son ........................ G01N 33/18
(Continued)

FOREIGN PATENT DOCUMENTS

JP    H03-288586 A    12/1991
JP    H06-262198 A    9/1994
(Continued)

OTHER PUBLICATIONS

PCT/ISA/210, "International Search Report for International Application No. PCT/JP2015/060318".
(Continued)

*Primary Examiner* — Jewel V Dowtin
(74) *Attorney, Agent, or Firm* — Manabu Kanesaka

(57) ABSTRACT

Provided are a concentration-factor measurement device and method for accurately calculating a concentration factor of circulating water, and a method for measuring a water-quality index value of the circulating water. The concentration-factor measurement device includes a light-absorbance measurement unit (1) for measuring absorbance by irradiating each of cells (12A-12C) with light, and an electrode measurement unit (2) equipped with electrodes (16, 17) that are inserted into a water sample in a container (20). For each item of water quality, the device calculates a concentration factor on the basis of a measured value measured when the water sample (W) is the circulating water, and a measured value measured when the water sample (W) is makeup water. A plurality of concentration factors are calculated on the basis of the measured values for plural items of water quality. Hence an accurate concentration factor can be obtained.

10 Claims, 6 Drawing Sheets

(56) References Cited

U.S. PATENT DOCUMENTS

| | | | | |
|---|---|---|---|---|
| 9,791,427 B2* | 10/2017 | Mori | ............ | G01N 33/442 |
| 2009/0123340 A1* | 5/2009 | Knudsen | ............ | G01N 33/1886 |
| | | | | 422/105 |
| 2009/0173629 A1* | 7/2009 | Kidwell | ............ | G01N 27/3335 |
| | | | | 204/415 |
| 2010/0082265 A1* | 4/2010 | Song | ............ | C02F 1/008 |
| | | | | 702/25 |
| 2012/0015445 A1* | 1/2012 | Kellner | ............ | G01N 21/6428 |
| | | | | 436/172 |
| 2017/0038358 A1* | 2/2017 | Mori | ............ | G01N 33/1853 |
| 2017/0234848 A1* | 8/2017 | Cheng | ............ | G01N 21/17 |
| | | | | 73/61.41 |
| 2017/0254752 A1* | 9/2017 | Palassis | ............ | G01N 21/59 |

FOREIGN PATENT DOCUMENTS

| | | | |
|---|---|---|---|
| JP | 2001-062263 A | 3/2001 | |
| JP | 2001-205249 A | 7/2001 | |
| JP | 2002-210454 A | 7/2002 | |
| JP | 2007-128440 A | 5/2007 | |
| JP | 2007-256147 A | 10/2007 | |
| JP | 2008-058148 A | 3/2008 | |
| JP | 2014-228488 A | 5/2013 | |
| WO | WO 2008058148 A2 * | 5/2008 | ............ C02F 1/4604 |

OTHER PUBLICATIONS

Japanese Office Action of JP Application No. 2014-086543 dated Jun. 30, 2015.

Shinichi Takasaki, "Kucho Setsubi-yo Haikankei no Boshoku to Kanri 3. Corrosion and water Quality", Refrigeration, 2002, vol. 77, No. 897, pp. 577 to 583.

\* cited by examiner

CONCENTRATION-FACTOR MEASUREMENT DEVICE AND METHOD

FIELD OF INVENTION

The present invention relates to a device and a method for measuring a concentration factor in a system for circulating water, such as cooling water or boiler water. The present invention also relates to a method for measuring a water-quality index value in the circulating water system.

BACKGROUND OF INVENTION

In a variety of factories, buildings, etc., a water system including various heat exchangers, e.g., refrigerating machines, is installed, and an object to be cooled is cooled by contacting circulating water (cooling water) and the object to be cooled with each other through the heat exchanger. Recently, in a circulating water system, it has been prevalent to operate the system under a condition of holding the circulating water at a higher concentration for the purpose of saving water. Under such an operating condition, however, an ion component is concentrated with evaporation of the circulating water, thus resulting in a possibility that scale may precipitate and adhere to the interior of the refrigerating machine.

With scale adhering to the interior of the refrigerating machine, heat transfer to the circulating water from the object to be cooled is impeded. Such a situation may lead to an event that a condensation degree of the object to be cooled reduces and pressure rises in a condenser, or that the load of a compressor increases with a rise of temperature of the object to be cooled, thus causing high-pressure cutout (i.e., stop of the compressor at pressure in excess of a certain level). Furthermore, the adhesion of scale reduces the refrigeration capability of the refrigerating machine, thereby increasing power consumption and reducing energy efficiency. It is hence required to appropriately perform concentration management in the circulating water system, and to suppress the precipitation of scale.

Generally, various water treatment chemicals are added into the circulating water system to prevent or reduce the occurrence of scale, slime, and corrosion. For example, there is known a method of controlling the concentration of a water treatment chemical, which is present in circulating water, by measuring the concentration of an organic substance contained in the circulating water, and by determining an added amount of the water treatment chemical on the basis of a measured value (see Patent Literature 1). There is also known a method of performing concentration management in the circulating water system by setting a threshold for electrical conductivity of the circulating water, and by executing an operation of reducing a concentration factor (such as increasing a blowing rate or injecting makeup water) when the electrical conductivity exceeds the threshold.

Here, the electrical conductivity of the circulating water is given as a value obtained by adding an electrical conductivity, which is resulted from multiplying an electrical conductivity attributable to components dissolved in the makeup water, by a concentration factor, and an electrical conductivity attributable to the chemicals added to the relevant water system. In other words, an accurate concentration factor cannot be obtained through a simple calculation of just by dividing the electrical conductivity of the circulating water by the electrical conductivity of the makeup water.

Patent Literature 1: Japanese Patent Publication 2002-210454 A

SUMMARY OF INVENTION

A concentration factor can also be calculated by measuring the concentration of an component dissolved in the circulating water and the concentration of the component dissolved the makeup water for one of targets selected from among calcium hardness, acid consumption (pH 4.8), and silica instead of electrical conductivity, and by executing calculation on the basis of measured values. However, when a component for which the dissolved concentration is measured adheres as scale to the heat exchanger and so on, or when such a component is precipitated in the circulating water system, a false concentration factor may be calculated. Thus, in the case of calculating the concentration factor only from the dissolved concentration of one component, there is a possibility that the circulating water system may be managed on the basis of the false concentration factor and the occurrence of a failure (abnormal state) cannot be detected quickly, whereby a countermeasure action may be delayed.

The present invention has been made in view of the above-described current situation of the related art, and an object of the present invention is to provide a concentration-factor measurement device and method for accurately calculating a concentration factor of circulating water, and a method for measuring a water-quality index value of the circulating water.

A concentration-factor measurement device of the present invention includes: an operating unit that is operated to select whether sample water is circulating water or makeup water; first to n-th (n is an integer of 2 or more) water quality measurement devices that measure first to n-th water-quality characteristic values of the sample water; and an arithmetic unit that calculates concentration factors on the basis of measured values measured by the water quality measurement devices for the circulating water and the makeup water.

In an embodiment of the present invention, the concentration-factor measurement device may include, as the water quality measurement devices, at least two among an optical measurement device for measuring transmittance or absorbance, one or two types of ion electrodes, and an electrical conductivity meter.

In an embodiment of the present invention, the operating unit, the first to n-th water quality measurement devices, and the arithmetic unit may be installed in one housing.

In an embodiment of the present invention, the housing may include insertion holes into which cells for optical measurement are formed. In this embodiment, a selection result display unit for displaying whether the sample water selected with the operating unit is the circulating water or the makeup may be disposed in the housing.

In an embodiment of the present invention, the concentration-factor measurement device may further include a measured-result display unit that displays at least the concentration factors among results measured on water quality and results measured on the concentration factors. In this embodiment, the concentration-factor measurement device may include a memory that stores the measured results, and the measured-result display unit may display trend information including past data.

The present invention may have an embodiment in which a sensor mounting panel being rotatable in a rising-up and laying-down direction is disposed in an upper surface portion of the housing, and the water quality measurement device constituted by each ion electrode or the electrical conductivity meter is mounted to the sensor mounting panel such that the water quality measurement device projects from a lower surface of the sensor mounting panel; a container for the sample water is disposed in the housing under the sensor mounting panel that is positioned in a laid-down state; and a lower end of the water quality measurement device is immersed in the sample water within the sample water container when the sensor mounting panel is positioned in the laid-down state.

In an embodiment of the present invention, the concentration-factor measurement device may include a plurality of measurement device sets each of which is constituted by the first to n-th water quality measurement devices.

A concentration-factor measurement method for circulating according to an embodiment of the present invention includes a step of calculating a concentration factor of the circulating water by the concentration-factor measurement device of the present invention.

A water-quality-index-value measurement method for circulating water according to an embodiment of the present invention includes steps of, by the concentration-factor measurement device of the present invention, measuring pH, electrical conductivity, calcium hardness, and acid consumption (pH 4.8) of the circulating water, and calculating at least one of a Langelier index and a Ryznar Stability Index on the basis of measured results.

A water-quality-index-value measurement method for circulating water according to an embodiment of the present invention includes steps of, by the concentration-factor measurement device of the present invention, measuring a sulfate ion concentration, an acid consumption (pH 4.8), and an acid consumption (pH 8.3) of the circulating water, and calculating a Mattsson ratio on the basis of measured results.

Advantageous Effects of Invention

According to the present invention, plural items of water quality are measured for the circulating water and the makeup water, and the concentration factor is calculated on the basis of the measured results for each item of water quality. The concentration factors calculated on the basis of the measured values for the plural items of water quality are compared with each other to select one item of water quality, which is appropriate for calculating the concentration factor. When there are plural items of water quality each appropriate for calculating the concentration factor, the concentration factor of the circulating water can be accurately determined by averaging the concentration factors calculated for the plural items of water quality. Concentration management of a circulating water system can be adequately performed by employing the concentration factors that have been determined as described above.

In the concentration-factor measurement device of the present invention, the operating unit, the water quality measurement devices, and the arithmetic unit may be installed in one housing such that the concentration-factor measurement device can be easily carried to a field site. A communication function may be incorporated in the housing to send data to a management center.

By displaying, on a display unit, whether the sample water is the circulating water or the makeup water, it is possible to avoid, e.g., mix-up of the sample water. Furthermore, by displaying the measured results on the display unit, a user can immediately recognize the measured results. By disposing the memory that stores the measured results, and by displaying a trend of the measured results on the display unit, the water management of the water system can be performed more adequately.

Measurement can be quickly performed with the features of disposing, in the housing, the sensor mounting panel that is rotatable to be raised up and laid down, mounting the water quality measurement devices to the sensor mounting panel, and performing the measurement in a state where lower ends of the water quality measurement devices are immersed in the sample water within the sample water container. Moreover, it is easier to wash the measurement devices and to load or unload the sample water container by bringing the sensor mounting panel into the raised-up state.

According to the present invention, with the feature of providing a plurality of measurement device sets each of which is constituted by the first to n-th water quality measurement devices, water quality can be measured for the circulating water and the makeup water at the same time.

According to the present invention, the concentration-factor measurement device may be used to measure the pH, the electrical conductivity, the calcium hardness, and the acid consumption (pH 4.8), and to calculate the Langelier index, which is an index indicating corrosivity of metal materials constituting pipes, heat exchangers, etc. in a water system, and/or the Ryznar Stability Index, which is an index indicating a tendency to generate scale, on the basis of the measured results.

According to the present invention, the concentration-factor measurement device may be used to measure the sulfate ion concentration, the acid consumption (pH 4.8), and the acid consumption (pH 8.3), and to calculate the Mattsson ratio, which is an index for the occurrence of pitting corrosion of copper, on the basis of the measured results.

DESCRIPTION OF EMBODIMENTS

An embodiment of the present invention will be described in detail below.

Figure 1:
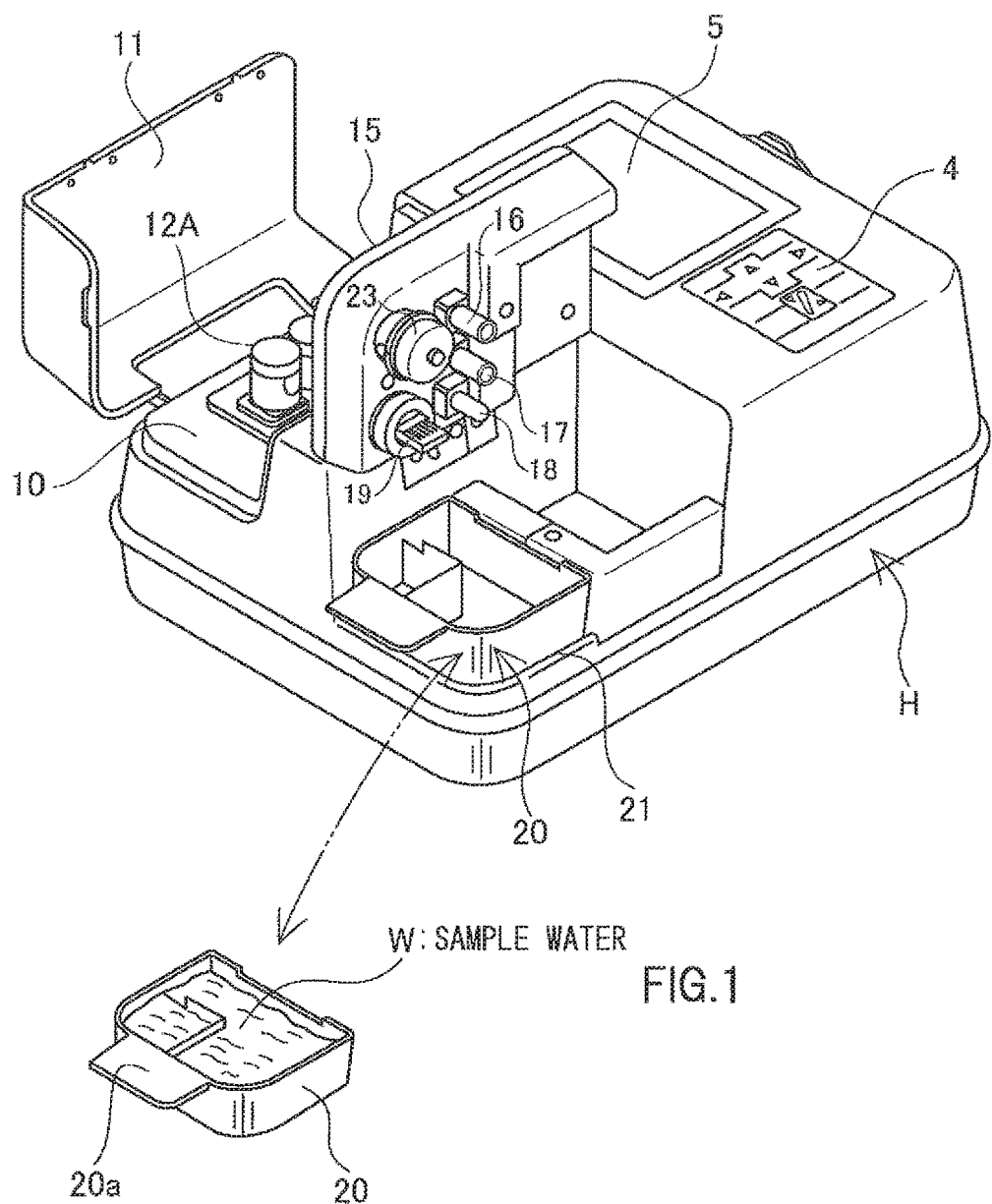
FIG. 1 is an external perspective view of a concentration-factor measurement device according to an embodiment of the present invention.
Figure 2:
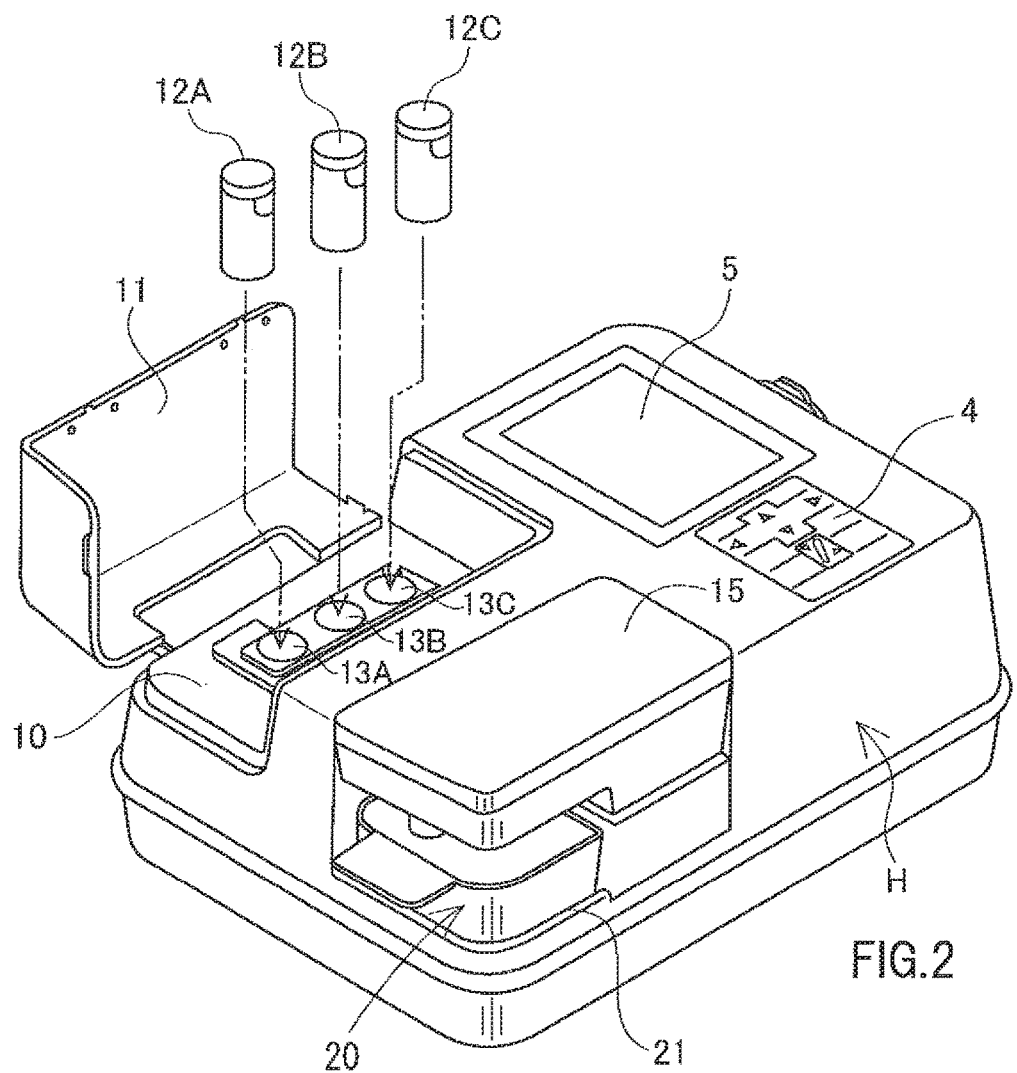
FIG. 2 is a perspective view referenced to explain a water quality measurement method using the concentration-factor measurement device illustrated in FIG. 1.
Figure 3:
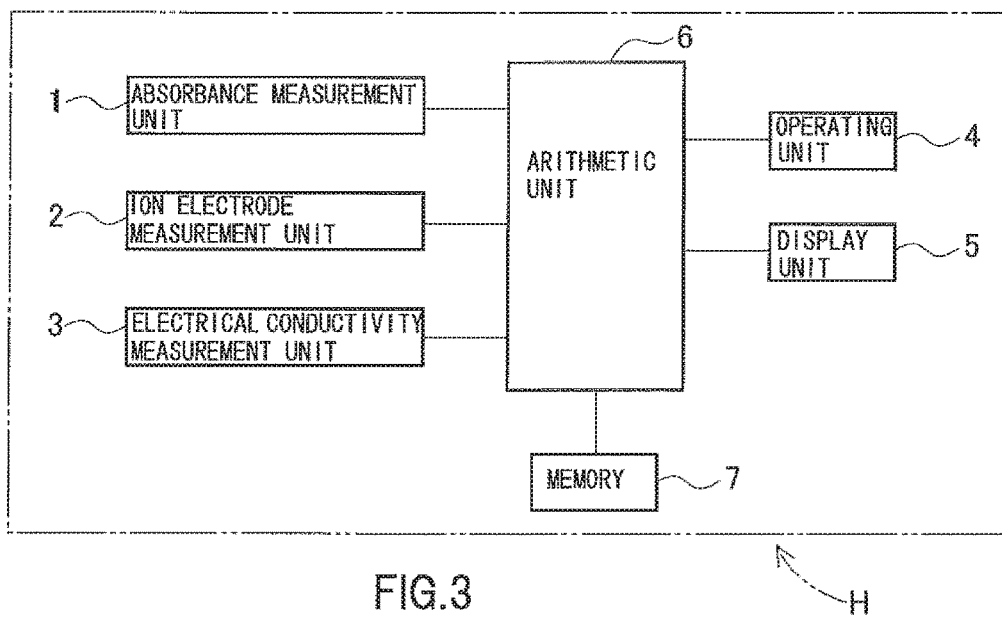
FIG. 3 is a block diagram of the concentration-factor measurement device illustrated in FIG. 1.

FIGS. 1 and 2 are each an external perspective view of a concentration-factor measurement device according to an embodiment of the present invention, and FIG. 3 is a block diagram of the concentration-factor measurement device. As illustrated in FIG. 3, the concentration-factor measurement device includes an absorbance measurement unit 1, an electrode measurement unit 2, an electrical conductivity measurement unit 3, an operating unit 4, a display unit 5, an arithmetic unit 6, and a memory 7. Those units 1 to 6 and the memory 7 are installed in a housing H.

As illustrated in FIGS. 1 and 2, the housing H is in the form of a synthetic resin case having a substantially rectangular parallelepiped shape. The operating unit 4 and the display unit 5, the latter being made of, e.g., a liquid crystal display, are disposed in one half of an upper surface of the housing H. The operating unit 4 is constituted by buttons, switches, a touch panel, etc., which are operated by a user.

In the other half of an upper surface of the housing H, a cell placement portion 10 is provided in the form of recessed steps and is covered with a cover 11 that can be turned to open and close the cell placement unit 1. In the other half of an upper surface of the housing H, a placement portion 21 for a sample water container 20 is further provided and a sensor mounting panel 15 is disposed above the placement portion 21 to be rotatable upward in a rising direction. The cover 11 and the sensor mounting panel 15 are each rotatably attached to the housing H with the aid of a hinge.

Insertion holes 13A, 13B and 13C for absorbance measurement cells (optical measurement device) 12A, 12B and 12C are provided in the cell placement portion 10. A light emitting element, a spectrometer, and a light receiving element are disposed within the housing H on both the sides of each of the insertion holes 13A to 13C in an opposing relation. The spectrometer may be omitted in some cases. Specified amounts of coloring reagents are previously enclosed in the cells 12A to 12C. The coloring reagents enclosed in the cells 12A to 12C are types different from one another.

The coloring reagents are different depending on components (targets) to be measured. For example, when the component to be measured is silica, a coloring reagent containing molybdenum can be used. When the acid consumption (pH 4.8) is measured, a coloring reagent containing Bromophenol blue can be used. When the acid consumption (pH 8.3) is measured, a coloring reagent containing phenolphthalein can be used. When a sulfate ion is measured, a coloring reagent containing barium chromate can be used.

After opening caps of the cells 12A, 12B and 12C and pouring the specified amounts of sample waters into the cells 12A, 12B and 12C, the caps are closed, and the sample water and the coloring reagent are mixed with each other in each cell. The cells 12A, 12B and 12C are then inserted into the insertion holes 13A, 13B and 13C, respectively. In that state, absorbance can be measured. The absorbance measurement unit 1 is constituted by the cells 12A to 12C, the light emitting elements, the spectrometers, the light receiving elements, drive circuits for those light emitting and receiving elements, and a processing circuit for a received light signal.

The sensor mounting panel 15 is rotatable in a vertical direction with the aid of a hinge to take a raised-up state illustrated in FIG. 1 or a laid-down state illustrated in FIG. 2. Not only ion electrodes 16 and 17, a PH glass electrode 18, and a reference electrode 23 constituting the electrode measurement unit 2, but also an electrical conductivity meter 19 constituting the electrical conductivity measurement unit 3 are mounted to the sensor mounting panel 15 such that respective lower ends of the above-described members project downward from a lower surface of the sensor mounting panel 15 in the laid-down condition.

In this embodiment, the ion electrode 16 is a bication selective electrode, and the ion electrode 17 is a calcium ion selective electrode.

The sample water container 20 is arranged under the sensor mounting panel 15 in the laid-down state at such a position as allowing the respective lower ends of the ion electrodes 16 and 17, the PH glass electrode 18, the reference electrode 23, and the electrical conductivity meter 19 to be immersed in the sample water W (see FIG. 1) within the container 20 when the sensor mounting panel 15 is laid down. The sample water container 20 has a grip 20a, and a user can load or unload the container 20 into or from the container placement portion 21 in the housing H while grasping the grip 20a by a hand. Moreover, protective caps for the above-mentioned various electrodes can be stored in a space S adjacent to the container 20.

The light emitting element used in the absorbance measurement unit 1 may be, e.g., an LED, a xenon flash lamp, or a halogen lamp. The spectrometer may be a filter such as an interference filter or a colored glass filter, a prism made of, e.g., a quartz crystal or molten quartz, or a grating such as a plane grating or a concave grating. The light receiving element is, e.g., a photodiode, and it converts light having transmitted through a sample to an electrical signal. The absorbance is determined from both the intensity of the transmitted light on the basis of the converted electrical signal and the intensity of light incident on the sample. It is to be noted that, in the present invention, transmittance may be determined instead of absorbance.

A calibration curve is prepared in advance by measuring the absorbance of a standard solution of the component to be measured, and data of the calibration curve is stored in the memory 7. The dissolved concentration of the component, which is present in the sample water and is to be measured, can be determined from the calculated absorbance by referring to the calibration curve. The absorbance and the dissolved component concentration may be calculated by an arithmetic unit (not illustrated) in the absorbance measurement unit 1, or by the arithmetic unit 6.

The ion selective electrode and the reference electrode constituting the electrode measurement unit 2 have high selectivity for an ion to be measured, and generate a potential depending on the ion concentration (i.e., the dissolved component concentration). The ion selective electrode constitutes a cell in combination with the reference electrode, and an electromotive force (potential difference generated between both the electrodes) E is measured by a potentiometer. Assuming that an electrode potential difference at the ion selective electrode is denoted by $E_{ind}$, an electrode potential difference at the reference electrode is denoted by $E_{ref}$, and a potential difference between the sample water W and the reference electrode is denoted by $E_j$, the electromotive force E is expressed by the following mathematical formula 1.

$$E = E_{ind} - E_{ref} + E_j \quad \text{(Math. 1)}$$

Here, $E_{ref}$ takes a constant value, and $E_j$ is ignorable with use of an appropriate salt bridge. Therefore, E is determined depending on only a value of $E_{ind}$, and the ion concentration to be measured can be expressed using the electromotive force of the above-mentioned cell. By previously determining a relation (calibration curve) between the ion concentration and the interelectrode potential difference with use of the standard solution, the concentration of the ion, which is present in the sample and is to be measured, can be determined from the measured value of the potentiometer. For example, total hardness (total hardness=calcium hardness+magnesium hardness) can be determined by employing the bication selective electrode 16 and the reference electrode 23. Furthermore, the calcium hardness can be determined by employing the calcium ion selective electrode 17 and the reference electrode 23. Data of the calibration curve is stored in the memory 7. The ion concentration to be measured may be calculated by an arithmetic unit (not illustrated) in the electrode measurement unit 2, or by the arithmetic unit 6.

The pH glass electrode 18 and the reference electrode 23 both constituting the electrode measurement unit 2 measure the pH of the sample water W by the so-called glass electrode method. In more detail, the pH is obtained by measuring the potential difference between the pH glass electrode 18, which is made of a special glass film sensitive to the activity of hydrogen ion, and the reference electrode 23, which exhibits a constant potential regardless of pH, with the potentiometer.

The electrical conductivity meter 19 constituting the electrical conductivity measurement unit 3 measures the electrical conductivity of the sample water W by the so-called AC two-electrode method. In more detail, the electrical conductivity is measured by applying an AC voltage between a pair of electrodes from an AC power supply, measuring a current flowing at that time with an AC ammeter, and by determining the solution resistance of the sample water W. The electrodes are made of, e.g., stainless steel or platinum. In addition, a temperature sensor, such as a resistance thermometer, is built in the electrical conductivity meter 19.

Figure 4:
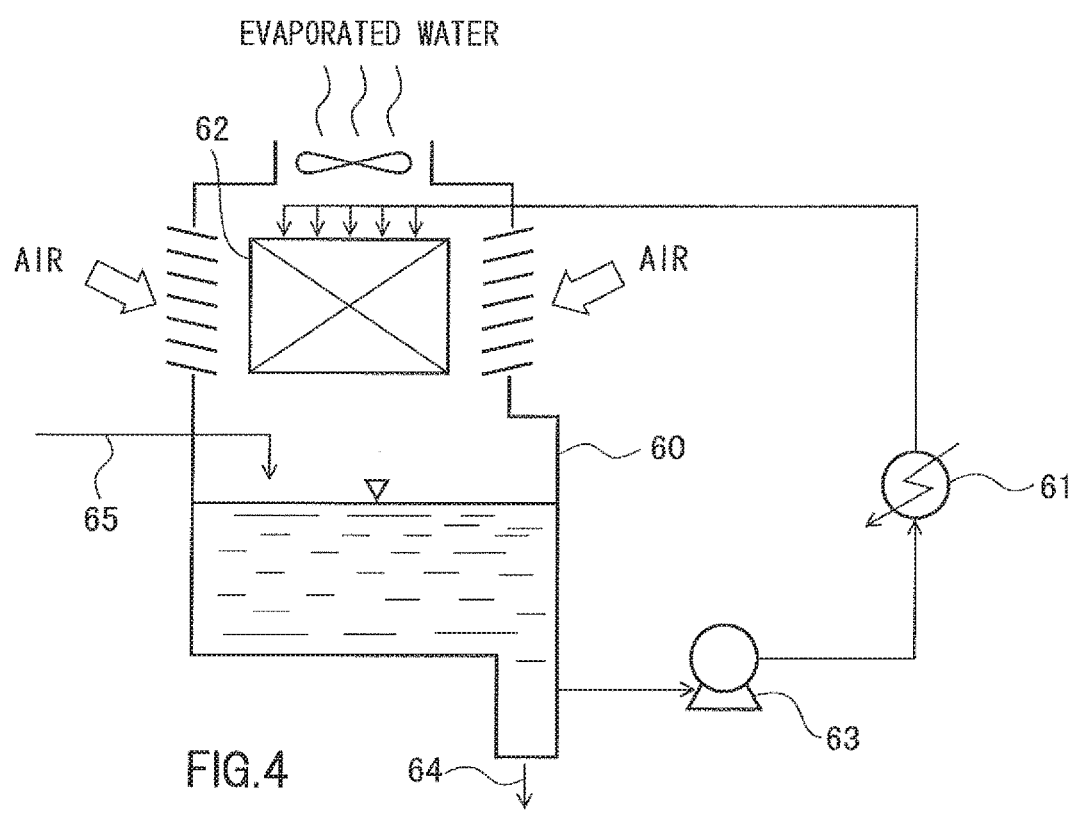
FIG. 4 illustrates a configuration of a circulatory cooling water system.

The sample water W contained in the cells 12A to 12C and the sample water container 20 is circulating water or makeup water in a circulatory cooling water system. FIG. 4 illustrates one example of water flow in the circulatory cooling water system. As illustrated in FIG. 4, water of which temperature has been raised through heat exchange in a heat exchanger 61 is supplied to a cooling column 60. Hot water supplied to the cooling column 60 flows down through a filled material 62, and part of the hot water evaporates through countercurrent contact with air. Water having been cooled by the latent heat of evaporation is stored in a pit in a lower portion of the cooling column 60 and is supplied to the heat exchanger 61 by a pump 63. Blowing is made by opening a blow valve (not illustrated) in a blow water pipe 64. The makeup water in amount corresponding to a total of an amount of evaporation and an amount of blow water is supplied to the cooling column 60 from a makeup water pipe 65 through a ball tap (not illustrated).

Sample water of the circulating water is obtained by sampling the water within the pit of the cooling column 60, water supplied to the heat exchanger 61 by the pump 63, or water supplied to the cooling column 60 from the heat exchanger 61, preferably part of the water within the pit. Furthermore, sample water of the makeup water is obtained by sampling part of the makeup water supplied to the cooling column 60 through the pipe 65.

The operating unit 4 in the concentration-factor measurement device is operated to set a circulating water mode and a makeup water mode in a switching manner. When the circulating water mode is set, values measured by the absorbance measurement unit 1, the electrode measurement unit 2, and the electrical conductivity measurement unit 3 are stored in the memory 7 as the measured values of the circulating water. When the makeup water mode is set, values measured by the absorbance measurement unit 1, the electrode measurement unit 2, and the electrical conductivity measurement unit 3 are stored in the memory 7 as the measured values of the makeup water.

The arithmetic unit 6 calculates a concentration factor, i.e., an index indicating how many times the salt concentration in the circulating water is higher than that in the makeup water, on the basis of the values measured when the circulating water mode is set and the values measured when the makeup water mode is set. For example, the concentration factor is calculated, for the same dissolved component, by dividing the dissolved component concentration measured when the circulating water mode is set, by the dissolved component concentration measured when the makeup water mode is set. In another example, the concentration factor can also be calculated by dividing the electrical conductivity measured when the circulating water mode is set, by the electrical conductivity measured when the makeup water mode is set.

In this embodiment, a plurality of concentration factors are obtained. More specifically, concentration factors on the basis of the dissolved component concentrations determined from respective absorbance values measured on the cells 12A to 12C, concentration factors on the basis of the ion concentrations determined from the values measured using the ion electrodes, and a concentration factor on the basis of the electrical conductivity are calculated.

The display unit 5 displays the plurality of concentration factors calculated by the arithmetic unit 6, and the values measured by the various measurement units. The memory 7 stores the values measured by the measurement units, the data of the calibration curve, the plurality of concentration factors calculated by the arithmetic unit 6, and so on.

Figure 5:
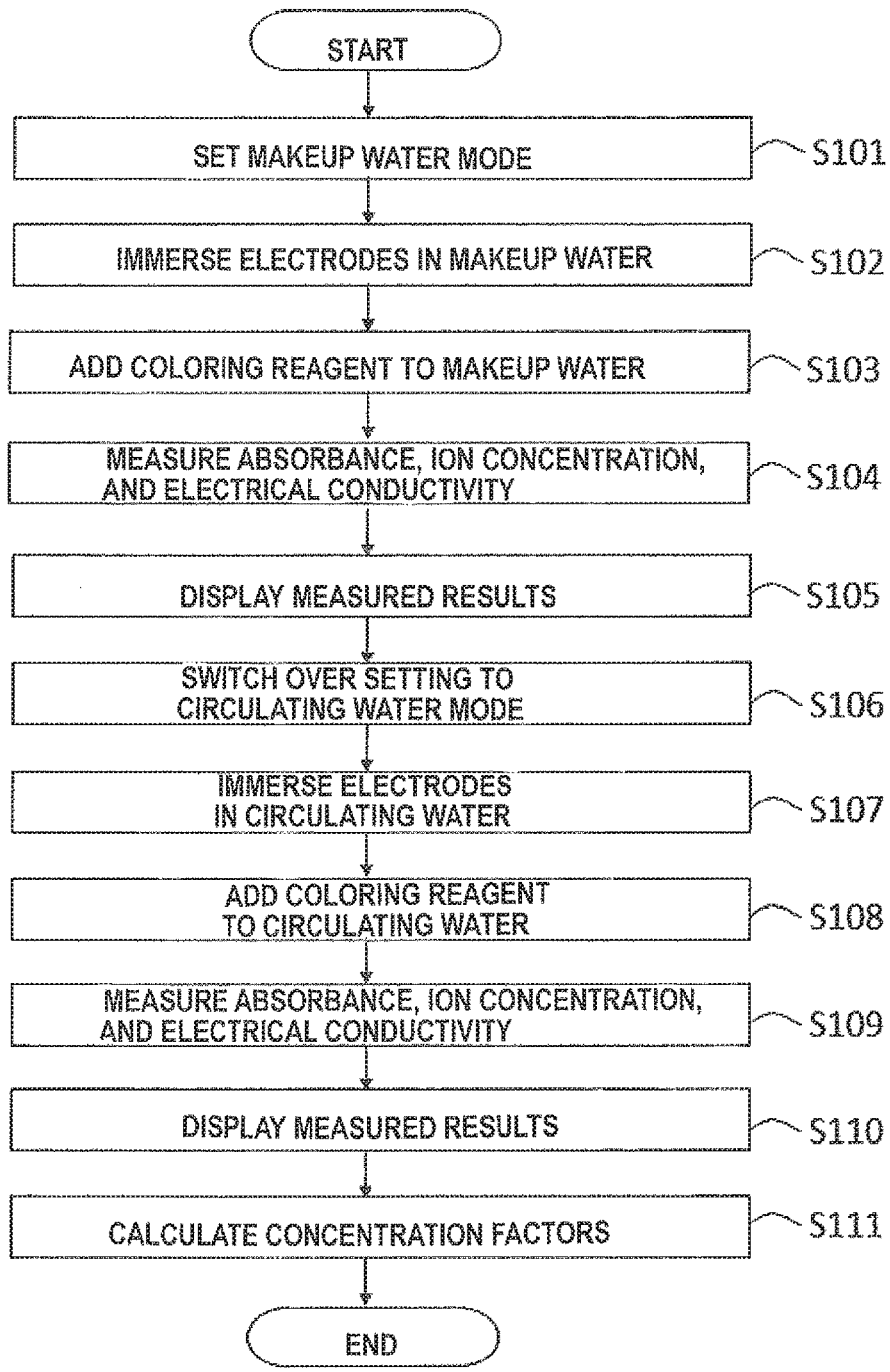
FIG. 5 is a flowchart referenced to explain a concentration-factor measurement method according to an embodiment of the present invention.

A concentration-factor measurement method according to this embodiment will be described below with reference to a flowchart illustrated in FIG. 5. The following description is made in connection with the case of performing the measurement for the circulating water after performing the measurement for the makeup water. However, the measurement for the makeup water may be performed after performing the measurement for the circulating water. As an alternative, values having been measured for the makeup water and stored in the memory 7 in the past may be referred to instead of performing the measurement for the makeup water.

Step S101: The makeup water mode is set with the operating unit 4.

Step S102: The sampled makeup water is poured into the sample water container 20, and the sample water container 20 is placed in the container placement portion 21 of the housing H. When the sensor mounting panel 15 is laid down, the respective lower ends of the ion electrodes 16 and 17, the pH glass electrode 18, the reference electrode 23, and the electrical conductivity meter 19 are immersed in the sample water within the sample water container 20.

Step S103: The sampled makeup water is poured into the cells 12A to 12C, and is sufficiently mixed with the coloring reagent in each cell. The cells 12A to 12C are then inserted and set in the insertion holes 13A to 13C, respectively.

Step S104: The absorbance measurement unit 1 measures the absorbance of the sample water (in this case, the makeup water), to which the coloring reagent has been added, by absorption photometry. By referring to the calibration curve stored in the memory 7, the dissolved component concentration of each component to be measured is determined from the value measured by the absorbance measurement unit 1.

Furthermore, the electrode measurement unit 2 measures the concentration of the ion, which is present in the sample water (makeup water) and is to be measured, by the ion electrode method, and measures the pH of the sample water (makeup water) by the glass electrode method. In addition, the electrical conductivity measurement unit 3 measures the electrical conductivity of the sample water (makeup water) by the AC two-electrode method.

Step S105: The values measured and calculated in the step S104 are stored in the memory 7 and are displayed on the display unit 5. Thereafter, the sensor mounting panel 15 is raised up, and the individual measurement devices are washed with pure water. Moreover, the sample water container 20 and the cells 12A to 12C are taken out.

Step S106: The setting is switched over from the makeup water mode to the circulating water mode with the operating unit 4.

Step S107: The circulating water sampled from the circulating water system is poured into the sample water container 20, the sample water container 20 is placed in the container placement portion 21, and the sensor mounting panel 15 is laid down.

Step S108: The circulating water sampled from the circulating water system is poured into the cells 12A to 12C, and is sufficiently mixed with the coloring reagent in each cell. The cells 12A to 12C are then inserted and set in the insertion holes 13A to 13C, respectively.

Step S109: The absorbance measurement unit 1 measures the absorbance of the sample water (in this case, the circulating water). By referring to the calibration curve stored in the memory 7, the dissolved component concentration of each component to be measured is determined from the value measured by the absorbance measurement unit 1.

Furthermore, the electrode measurement unit 2 measures the concentration of the ion, which is present in the sample water (circulating water) and is to be measured, by the ion electrode method, and measures the pH of the sample water (circulating water) by the glass electrode method. In addition, the electrical conductivity measurement unit 3 measures the electrical conductivity of the sample water (circulating water).

Step S110: The values measured and calculated in the step S109 are stored in the memory 7 and are displayed on the display unit 5.

Step S111: The arithmetic unit 6 calculates the plurality of concentration factors by taking out, from the memory 7, not only the dissolved component concentrations, the electrical conductivity, etc., which have been measured during a period of the circulating water mode being set, but also the dissolved component concentrations, the electrical conductivity, etc., which have been measured during a period of the makeup water mode being set, and by executing divisions on the basis of the taken-out values. The plurality of calculated concentration factors are stored in the memory 7 and are displayed on the display unit 5.

Thus, in this embodiment, two or more items, more preferably three or more items, of different water quality characteristic values are measured and the plurality of concentration factors are calculated. Accordingly, for example, even when some component precipitates as scale and the concentration factor calculated on the basis of the measured value of the relevant component takes a large value, a highly-accurate concentration factor can be obtained from the values measured on the other items of water quality. In the case of calculating the concentration factor from only two items of water quality, it is preferable to avoid, for example, a combination of the acid consumption (pH 4.8) and the calcium hardness, the combination being anticipated to cause generation of calcium carbonate scale, and a combination of silica and the magnesium hardness, the combination being anticipated to cause generation of magnesium silicate scale. Moreover, it is also inadequate, in a system using a hypochlorite slime inhibitor, to perform the concentration management with use of a chloride ion. On the basis of the highly-accurate concentration factor obtained as described above, the concentration management of the circulating water system can be performed appropriately.

Figure 6:
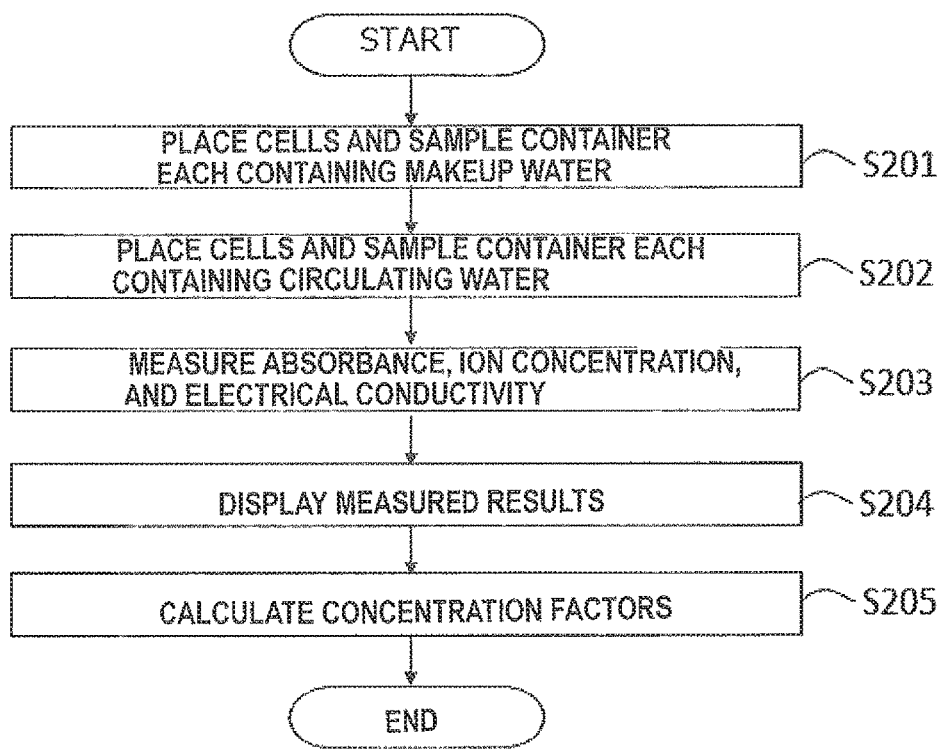
FIG. 6 is a flowchart referenced to explain another example of the concentration-factor measurement method.

In the above-described embodiment, as illustrated in FIG. 1, the concentration-factor measurement device includes only one measurement unit set that is constituted by the absorbance measurement unit 1, the electrode measurement unit 2, the electrical conductivity measurement unit 3, the sensor mounting panel 15, the sample water container 20, and the sample-water-container placement portion 21. However, the concentration-factor measurement device may include two or more measurement unit sets. In such a case, the water quality of the circulating water and the water quality of the makeup water can be measured at the same time without exchanging the two types of sample water. Furthermore, the operating unit 4 is not needed to have the function of switching over the setting between the circulating water mode and the makeup water mode. For each of the circulating water and the makeup water, two or more samples can be measured at the same time in parallel. A method for simultaneously measuring the circulating water and the makeup water with the concentration-factor measurement device in the above case will be described below with reference to a flowchart illustrated in FIG. 6.

Step S201: The makeup water supplied to the circulating water system is sampled and poured into one set of the cells 12A to 12C and the sample water container 20. Those cells and sample water container are placed in one measurement unit set, and the sensor mounting panel 15 is laid down.

Step S202: The circulating water sampled from the circulating water system is poured into the other set of the cells 12A to 12C and the sample water container 20. Those cells and sample water container are placed in the other measurement unit set, and the sensor mounting panel 15 of the other measurement unit set is laid down.

Step S203: The absorbance measurement unit 1 in each measurement unit set measures the absorbance of the sample water. By referring to the calibration curve stored in the memory 7, the dissolved component concentration of each component to be measured is determined for each of the circulating water and the makeup water from the value measured by the absorbance measurement unit 1. Furthermore, the electrode measurement unit 2 measures the concentration of the ion to be measured and the pH of the sample water. In addition, the electrical conductivity measurement unit 3 measures the electrical conductivity of the sample water.

Step S204: The values measured and calculated in the step S203 are stored in the memory 7 and are displayed on the display unit 5.

Step S205: The arithmetic unit 6 calculates the plurality of concentration factors by taking out, from the memory 7, not only the dissolved component concentrations, the electrical conductivity, etc. of the circulating water, but also the dissolved component concentrations, the electrical conductivity, etc. of the makeup water, and by executing divisions on the basis of the taken-out values. The plurality of calculated concentration factors are stored in the memory 7 and are displayed on the display unit 5.

Thus, the concentration factors can be more quickly calculated by providing two or more measurement unit sets.

The absorbance measurement unit 1, the electrode measurement unit 2, and the electrical conductivity measurement unit 3 are disposed in the above-described embodiment. In the present invention, however, one or two among those units may be omitted insofar as two or more items of water quality are measured. Even with such a configuration, the plurality of concentration factors can be determined from measurement data obtained for plural items of water quality.

In the present invention, the arithmetic unit 6 may calculate a Langelier index (saturation index) of the circulating water from the acid consumption (pH 4.8) measured by the absorbance measurement unit 1, the pH and the calcium hardness both measured by the electrode measurement unit 2, and the electrical conductivity measured by the electrical conductivity measurement unit 3. The Langelier index represents a difference between the pH of the circulating water and the saturation pH (pHs) of calcium carbonate, and it is an index of corrosivity of metal materials constituting pipes, heat exchangers, etc. in a water system. The pHs is determined from the following mathematical formula 2 by a simplified calculation method (Nordell method).

$$pHs = (9.3 + \text{value } A + \text{value } B) - (\text{value } C + \text{value } D) \quad \text{(Math. 2)}$$

Here, the value A is a value determined depending on the concentration of evaporation residues, and is calculated from the electrical conductivity. The value B is a value determined depending on the temperature of the circulating water. The value C is a value determined depending on the calcium hardness. The value D is a value determined depending on the acid consumption (pH 4.8).

Furthermore, the arithmetic unit 6 can calculate RSI (Ryznar Stability Index), which is an index of tendency for corrosion of water and generation of scale, from the following mathematical formula 3 on the basis of the pH of the circulating water and the saturation pH (pHs) of calcium carbonate.

$$RSI = 2pHs - pH \quad \text{(Math. 3)}$$

When RSI is less than 6, the index indicates that the water has a tendency to generate scale. When RSI is not less than 6 and less than 7, the index indicates that the water is in a stable state. When RSI is not less than 7, the index indicates that the water has a tendency to generate corrosion.

Moreover, the arithmetic unit 6 can determine a Mattsson ratio, which is an index for the occurrence of pitting corrosion of copper, on the basis of the concentration of sulfate ion, the acid consumption (pH 4.8), and the acid consumption (pH 8.3), which have been measured by the absorbance measurement unit 1. The Mattsson ratio represents a ratio of the concentration of hydrogencarbonate ion to the concentration of sulfate ion in water (i.e., $[HCO_3^-]/[SO_4^{2-}]$), and the concentration of hydrogencarbonate ion $HCO_3^-$ (mg $HCO_3^-$/L) can be determined from the following mathematical formula 4.

$$HCO_3^- (\text{mg } HCO_3^-/L) = 1.22 \times (\text{acid consumption (pH4.8)} - 2 \times \text{acid consumption(pH8.3)}) \quad \text{(Math. 4)}$$

When the Mattsson ratio is not more than 1 and residual chlorine is present, this state is judged as being apt to cause pitting corrosion of copper in hot water at about 60° C. (adapted from: JRA-GL02(1994) The Japan Refrigeration and Air Conditioning Industry Association).

Thus, with the concentration-factor measurement device according to this embodiment, water-quality index values, such as the Langelier index, the Ryzner Stability Index, and the Mattsson ratio, can be easily calculated from the values measured in the process of calculating the concentration factors.

Since the values measured and calculated in the concentration-factor measurement device are stored in the memory 7, trend information may be displayed on the display unit 5 by utilizing the stored values.

In the present invention, the concentration-factor measurement device may include a communication unit such that, after taking out the values measured and calculated in the concentration-factor measurement device from the memory 7, those values can be output to an external server. The communication unit may transmit data to the server via a wired/wireless network. As an alternative, a mobile terminal, e.g., a smartphone, may receive data from the communication unit via a wired/wireless network, and may transmit the received data to the server.

While, in the above-described embodiment, the display unit 5 displays the mode of circulating water or makeup water and the measured results, separate display units may be disposed to indicate them in different ways. In the latter case, whether the mode of circulating water or makeup water may be indicated with a lamp or voices.

EXAMPLE

Example 1

The electrical conductivity, the calcium hardness, the acid consumption (pH 4.8), and the silica concentration were measured for the circulating water and the makeup water in the circulating water system, which was installed in a model plant, by employing the concentration-factor measurement device illustrated in FIGS. 1 and 2. Furthermore, concentration factors were calculated from the measured values. The volume of each of the cells 12A to 12C was set to 4 mL. Bromocresol Green was used as the coloring reagent for measuring the acid consumption (pH 4.8), and ammonium molybdate was used as the coloring reagent for measuring silica. The measured results are listed in Table 1 given below.

TABLE 1

| Water Quality | Circulating Water | Makeup Water | Concentration Factor (Circulating Water/ Makeup Water) |
|---|---|---|---|
| Electrical Conductivity (mS/m) | 157 | 27 | 5.8 |
| Calcium Hardness (mg $CaCO_3$/L) | 270 | 52 | 5.2 |
| Acid Consumption (pH 4.8) (mg $CaCO_3$/L) | 240 | 45 | 5.3 |
| Silica (mg $SiO_2$/L) | 106 | 20 | 5.3 |

In this model plant, as listed in Table 1, the concentration factors calculated from respective values of the calcium hardness, the acid consumption (pH 4.8), and the silica concentration of the circulating water and the makeup water were almost the same, namely within the range of 5.2 to 5.3. Thus, the concentration factor was determined to be 5.3 by taking an average of the calculated values of the concentration factors.

On the other hand, the concentration factor calculated from the electrical conductivity was 5.8, namely slightly larger than the concentration factors calculated from the dissolved component concentrations. The above result is thought as being caused by a rise of the electrical conductivity attributable to the chemicals. Accordingly, the following point was proved; namely, it is appropriate to calculate the concentration factor on the basis of the dissolved component concentration in this model plant.

Furthermore, in this model plant, because the temperature at a circulating-water outlet of a heat exchanger was 40° C.

and the pH of the circulating water in a process of analyzing water quality was 8.7, the Langelier index was calculated to be 1.0. From the above result, the following point was ascertained at a field site; namely, in the circulating water system in this model plant, precipitation of calcium carbonate tends to occur and a tendency of corrosion of water is slight.

When the Langelier index is calculated without employing the concentration-factor measurement device, it is required to take back sample water, and to perform, for example, the steps of analyzing the sample water (or sending the sample water to a water-quality analysis company in some cases), and calculating the Langelier index from the obtained individual values. Therefore, the number of days ranging from several days to about one week is needed for the process of sampling the water and finally calculating the Langelier index. Thus, the calculated Langelier index is different from the actual Langelier index at the time of the calculation, and the circulating water system cannot be managed appropriately.

The present invention has been described in detail in connection with the particular embodiment. It is, however, apparent that the present invention can be variously modified without departing from the purport and the scope of the present invention.

This application is based on Japanese Patent Application No. 2014-086543 filed on Apr. 18, 2014, the entire contents of which are incorporated herein by reference.

The invention claimed is:

1. A concentration-factor measurement device, comprising
    an operating unit that is operated to select whether sample water is circulating water or makeup water;
    first to n-th (n is an integer of 2 or more) water quality measurement devices that measure first to n-th water-quality characteristic values of the sample water; and
    an arithmetic unit that calculates concentration factors on the basis of measured values measured by the water quality measurement devices for the circulating water and the makeup water,
    wherein the operating unit, the first to n-th water quality measurement devices, and the arithmetic unit are installed in one housing,
    a sensor mounting panel being rotatable in a rising-up and laying-down direction is disposed in an upper surface portion of the housing, and the water quality measurement device constituted by each ion electrode or the electrical conductivity meter is mounted to the sensor mounting panel such that the water quality measurement device projects from a lower surface of the sensor mounting panel,
    a container for the sample water is disposed in the housing under the sensor mounting panel that is positioned in a laid-down state, and
    a lower end of the water quality measurement device is immersed in the sample water within the sample water container when the sensor mounting panel is positioned in the laid-down state.

2. The concentration-factor measurement device according to claim 1, wherein the concentration-factor measurement device includes, as the water quality measurement devices, at least two among an optical measurement device for measuring transmittance or absorbance, one or two types of ion electrodes, and an electrical conductivity meter.

3. The concentration-factor measurement device according to claim 1, wherein the housing has insertion holes into which cells for optical measurement are formed.

4. The concentration-factor measurement device according to claim 1, wherein a selection result display unit for displaying whether the sample water selected with the operating unit is the circulating water or the makeup water is disposed in the housing.

5. The concentration-factor measurement device according to claim 1, further comprising a measured-result display unit that displays at least the concentration factors among results measured on water quality and results measured on the concentration factors.

6. The concentration-factor measurement device according to claim 5, further comprising a memory that stores the measured results,
    wherein the measured-result display unit displays trend information including past data.

7. The concentration-factor measurement device according to claim 1, wherein the concentration-factor measurement device includes a plurality of measurement device sets each of which is constituted by the first to n-th water quality measurement devices.

8. A concentration-factor measurement method for circulating water, the method comprising a step of calculating a concentration factor of the circulating water by the concentration-factor measurement device according to claim 1.

9. A water-quality-index-value measurement method for circulating water by a concentration-factor measurement device comprising
    an operating unit that is operated to select whether sample water is circulating water or makeup water;
    first to n-th (n is an integer of 2 or more) water quality measurement devices that measure first to n-th water-quality characteristic values of the sample water; and
    an arithmetic unit that calculates concentration factors on the basis of measured values measured by the water quality measurement devices for the circulating water and the makeup water,
    the method comprising:
    measuring pH, electrical conductivity, calcium hardness, and acid consumption (pH 4.8) of the circulating water, and
    calculating at least one of a Langelier index and a Ryznar Stability Index on the basis of measured results.

10. A water-quality-index-value measurement method for circulating water by a concentration-factor measurement device comprising
    an operating unit that is operated to select whether sample water is circulating water or makeup water;
    first to n-th (n is an integer of 2 or more) water quality measurement devices that measure first to n-th water-quality characteristic values of the sample water; and
    an arithmetic unit that calculates concentration factors on the basis of measured values measured by the water quality measurement devices for the circulating water and the makeup water,
    the method comprising:
    measuring a sulfate ion concentration, an acid consumption (pH 4.8), and an acid consumption (pH 8.3) of the circulating water, and
    calculating a Mattsson ratio on the basis of measured results.

* * * * *